United States Patent
Ketteridge et al.

(10) Patent No.: US 8,114,067 B1
(45) Date of Patent: Feb. 14, 2012

(54) LASER INDUCED REDUCTION OF VISUAL ACUITY

(75) Inventors: Peter A. Ketteridge, Amherst, NH (US); Eric J. Gustafson, Brookline, NH (US); Evan P. Chicklis, Amherst, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 346 days.

(21) Appl. No.: 12/422,588

(22) Filed: Apr. 13, 2009

(51) Int. Cl.
*A61B 3/00* (2006.01)
*A61N 5/067* (2006.01)

(52) U.S. Cl. ............... 606/4; 250/492.1; 606/2; 372/25; 362/553; 362/259

(58) Field of Classification Search ............ 606/2, 3, 606/4, 5, 6, 10, 11, 12, 13, 14, 15; 372/25, 372/26; 250/492.1; 362/553, 109–120, 259
See application file for complete search history.

(56) References Cited

U.S. PATENT DOCUMENTS

| | | | | |
|---|---|---|---|---|
| 5,616,139 A * | 4/1997 | Okamoto | | 606/4 |
| 6,090,102 A * | 7/2000 | Telfair et al. | | 606/10 |
| 6,799,868 B2 * | 10/2004 | Brown et al. | | 362/259 |
| 7,040,780 B2 * | 5/2006 | Diehl | | 362/259 |
| 7,784,390 B1 * | 8/2010 | Lowell et al. | | 89/1.11 |
| 2006/0100677 A1 * | 5/2006 | Blumenkranz et al. | | 607/89 |
| 2008/0167835 A1 * | 7/2008 | Zank et al. | | 702/151 |
| 2010/0172136 A1 * | 7/2010 | Williamson et al. | | 362/259 |
| 2010/0237258 A1 * | 9/2010 | Welch et al. | | 250/492.1 |

OTHER PUBLICATIONS

Venkatesh et al., Thermal lens measurements in the cornea, 1985, British journal of Ophthalmology, 69, p. 92-95.*

* cited by examiner

*Primary Examiner* — Sam Yao
*Assistant Examiner* — Andrew Sandefer
(74) *Attorney, Agent, or Firm* — Daniel J. Long; Robert K. Tendler

(57) ABSTRACT

A system for laser induced reduction of visual acuity suitable for crowd control and disabling of individuals uses an eye-safe pulsed IR source in which a laser beam is imaged onto the cornea of an individual to heat the cornea, thereby to cause defocusing and disorientation.

15 Claims, 8 Drawing Sheets blurred image

LASER INDUCED REDUCTION OF VISUAL ACUITY

FIELD OF THE INVENTION

This invention relates to non-lethal weapons technology and more particularly to the utilization of pulsed infrared radiation to disable an individual for the purpose of crowd control, or perimeter personnel incapacitation.

BACKGROUND OF THE INVENTION

Non-lethal weapons technology has been utilized for incapacitating individuals for the purposes of for instance, crowd rejection or perimeter personnel control. One would like to be able to prevent people from attacking or harassing individuals so that they cannot get any closer than one would like for personal safety. In the past, systems have utilized RF waves to make an individuals skin feel as if it is burning up; and some systems utilize short intense laser beams which irradiate the skin to make one think that the skin is burning.

Crowd control has also been attempted utilizing acoustic means for projecting loud music or sounds. However, such systems require an inordinate amount of antenna space and power. While lasers are good because one can focus the beam very precisely and projected with pinpoint accuracy and high powered lasers are not eye-safe and can be dangerous, especially with unintended or accidental deployment of a laser beam.

Thus, laser beams that are utilized to countermeasure people or systems cause permanent injury to individuals in the path of the laser beam.

Moreover, with respect to RF crowd control systems, the amount of power to dissuade a crowd is enormous and requires a very large antenna system to produce a focused RF beam at any reasonable distance. Such systems also require kilowatts of power because RF protons are very weak.

Additionally, for non-lethal crowd control and the like, so-called rubber bullets or tasers have been utilized as non-lethal means for such applications. However, rubber bullets can in fact do permanent damage and tasers have been known to so completely incapacitate an individual that permanent damage also occurs.

There is therefore a need to provide a non-lethal means for incapacitating individuals which results in temporary disorientation and discomfort without causing permanent damage to the individual.

Such systems short of permanently maiming or killing an individual are important to be able to interdict individuals not utilizing lethal weapons, such as individuals throwing rocks and the like at the police and military personnel.

By way of further background and more particularly with respect to eye-safe lasers, typical eye safety occurs at wavelengths roughly around 1.5 microns and longer. The reason that such wavelengths do not damage the eye is that the aqueous humor or vitreous humor of the eye contain close to 90% water that absorbs the laser beam before a laser beam can hit the retina. Note that it is the retina where nerve receptors of the eye are located and permanent damage can be done to the retina because once the retina has any nerve damage it is not repairable.

While 1.5 microns is considered to be in the near infrared, it is important to note that the eye generally shuts off at around 0.8 microns so that anything that is almost twice as long will not be observable by the naked eye. When one reaches 0.8 microns images become extremely red and all of a sudden they simply disappear once one is in the infrared.

In laser systems for instance involving laser target designation, one does not simply want to spray friendlies with laser radiation that could damage their eyes.

For laser target designators or laser range finders the infrared band that one operates in is longer than the 1.5 micron radiation described above. Note that at 1.5 microns the energy of the waves is absorbed by the eye in a gradual fashion typically over a centimeter within the eye.

Thus for radiation in the 1.5 micron region as a beam comes in and hits the cornea, goes through the cornea and eventually in another couple of millimeters or a centimeter gets absorbed, there is no large temperature increase at the retina. In short, at 1.5 microns one does not have intense volumetric heat.

Having described various methods of incapacitating individuals, what is required is a safer and at the same time more disorienting method for crowd control or incapacitating individuals.

SUMMARY OF INVENTION

It has been found that by using a pulsed IR laser source at between 2.5 and 3 microns, when such a beam impinges on the human cornea differential lateral thermal expansion occurs across the cornea which causes the cornea to bulge out in the center more than it does at its periphery. It has been found that after a pulse of infrared energy the cornea returns to a thermal equilibrium after about $1/30^{th}$ of a second.

The result of distorting the cornea is that the individual's autonomic nervous system seeks to compensate for the initial distortion by deforming the lens behind the cornea until focus has been achieved. If one were to use a continuous wave or CW laser, all areas of the cornea would eventually arrive at the same temperature and no blurring or defocusing would occur at the retina.

However, with a pulsed laser beam the cornea never achieves lateral thermal equilibrium, and the eye is perpetually trying to refocus itself. This causes discomfort, with the result being that the first thing that the individual does is to cover his or her eyes. The lack of ability for an individual to focus prevents the individual from taking aggressive actions, with the 2.5 to 3 micron radiation not causing any permanent damage to the individual's eye. Thus, the subject system can be characterized as a non-lethal weapons technology.

It has been found that with a rise of $3°$ C. at the center of the cornea one temporarily bulges the cornea in such a manner that images at the retina are defocused into a grey diffused mat.

The 2.5 to 3 micron radiation can be generated by erbium lasers in which erbium in one embodiment is in the crystal, glass or other suitable host, namely an yttrium iron garnet crystal host commonly known as YAG among others. Note that these type of lasers emit at wavelengths compatible with fibers used to channel and focus the energy.

These lasers are direct emission lasers capable of putting out very high power at the proper wavelengths to maximize volumetric absorption which drives the magnitude of the defocusing noted above.

Note that in the design of the subject lasers, there is a certain amount of energy that is required to be delivered to the cornea. One wants to raise the temperature of the cornea by depositing a certain amount of energy at and just below the surface of the cornea. Therefore there needs to be a certain amount of fluence or watts per centimeter, or joules per square centimeter to be deposited on the cornea. The purpose of depositing this amount of energy is that one has to create a temperature gradient across the cornea which distorts the cornea and thus defocuses the image at the retina.

Prior to being irradiated the cornea has a gradient of zero. Thus, the entire eyeball is at the same ambient temperature. At an equilibrium the eye is at 300° K or 86° C. Thus, there is no gradient across the cornea prior to the cornea being irradiated.

It is the purpose of the subject invention to quickly deposit energy in the proper density so as to engender an instantaneous temperature gradient across from the center of the pupil to the edges where the heat sink is located. It is noted that the center or the cornea is harder than the edges.

Thus, if one is irradiating the eye at, for instance, a constant laser intensity, the eye will cool off more quickly at the edges and less quickly at the center because the center is further away from the heat sink. It has been found that a 3° centigrade rise in temperature provides sufficient defocusing for disorienting individuals.

The defocusing is a function of the change in focal length as a function of temperature and is also a function of the change of index of refraction with temperature. These two products create aberrations in optical components that are thermally loaded. By projecting a moderate amount of power onto the cornea one can engender large volumetric absorption which creates optical aberrations that result in defocusing.

Note that if the optic does no absorb any power there will be no aberrations formed because no thermal gradients will be generated.

Note also that as an optical element heats up, the optical power of the particular lens involved is changed because the material that the lens is made of has an index of refraction change with temperature. Typically one can look at the situation as involving the case that as a material gets more dense or less dense, the index of refraction changes. This of course is one of the factors that determines the focal power of the eye and indeed of any optical lens.

In essence, the optical system involving the cornea and the lens behind it can be characterized as water lenses; and water is known to absorb IR energy.

Unlike the laser utilized for instance to remove port whine stains in which one is intending to remove cells, in the subject case one is simply heating the cornea without removing cells.

Note in what is called an accommodated eye where the pupil has the diameter of about 6 or 7 millimeters, the amount of energy to be imparted to the eye in order to promote defocusing is about 50 to 75 millijoules per square centimeter. Thus one wants to deliver 50 millijoules to a person, or 100 millijoules for two eyes at 30 times a second.

The pulsing of the laser is important because every time the eye is successful in bringing the focus back one wants to impart another pulse of energy to the cornea to again distort the cornea and make sure that the defocusing is not compensated.

It has been found that the autonomic nervous system goes from a defocused to focused image in a fraction of a second, for instance $5/10^{ths}$ of a second.

Thus, the pulse repetition frequency or pulse of the laser would desirably be between 10 and 50 hertz.

In one embodiment, in order to provide enough fluence, lasers in the 10 watt range are used. The important thing for 10 watt lasers is that for significant ranges the laser should be a diffraction limited laser. This aides in delivering energy at longer distances at the proper fluence level.

While pencil thin laser beams may be useful and can be scanned electronically, it sometimes useful to provide beam shaping such that the optics at the output of the laser produces an instantaneous fan that spreads the beam over some predetermined sector. The result is that one can inject the beam into people of different heights and certainly people at different lateral locations. Note that beam fanning can be achieved through piezoelectric or motor controlled mirror systems which provide electro-optical scanning.

Taking for instance a 10 watt erbium laser at about 100 millijoules or 0.1 joule per square centimeter, one can generate thermal rises of a 3° C. even for a very broad beam, albeit it at shorter distances than would be effective for narrow beams.

Note that at the wavelengths described above laser power is deposited within a fraction of a millimeter such that the laser beam is absorbed in the cornea which on average is about a half a millimeter in thickness. Thus, radiation from the subject 2.1 to 3 micron source is absorbed within a fraction of a millimeter and within the 500 micron thick cornea, such that all of the energy at the above wavelength is absorbed within the cornea itself. Note that by irradiating the cornea, because it is constantly shedding cells and rebuilding itself, any damage to the cornea that could be generated by the subject system is repairable. This of course is not true for the nerves at the retina.

Note that the cornea is composed of a series of transparent cells called stoma cells, with these cells being transparent and mostly made up of water.

The cornea, upon being irradiated with the subject system bulges in that it deforms more at the center than it does at the sides of the cornea. This causes extreme aberrations primarily resulting in defocusing. Note that the cornea does not have its curvature changed uniformally, but rather because of the lateral differential heat transfer in the cornea the bulge produced by the radiation is non-uniform. It will be appreciated that if one loads an optic or perturbs it in any way that is non-uniform the focal quality is degraded.

Upon being irradiated by the subject system, the person sees images that become fuzzy or defocused. When the brain ascertains that an image is defocused, the autonomic nervous system drives the curvature of the lens behind the cornea in about a $30^{th}$ of a second. Thus it takes the brain about a $30^{th}$ of a second to drive the lens to a different curvature.

As mentioned before, the reason for the pulsing is that within a $30^{th}$ of a second the cornea cools, meaning that the thermal loading is relaxed. Thus the 3° C. thermal rise dissipates.

As a rule, if the temperature rise at the cornea exceeds 10° C., there may in fact be damage. Thus, it is important to the subject invention that the thermal rise be limited to less than 10° C.

In operation, upon delivery of the pulse, the instantaneous energy is delivered in microseconds and there is a lateral gradient set up across the cornea. The individual without any conscious effort wants to refocus. By the time the individual's brain controls the lens to a focus situation the lens is cooling off so that the autonomic nervous system can bring the image into focus after about a $30^{th}$ of a second. Thus upon radiation the individual is in a mode where the individual is trying to compensate for an aberration that is going away as he is trying to refocus.

Assuming that the individual is successful in refocusing after the initial pulse and assuming the second pulse arrives in a $30^{th}$ of a second his autonomic nervous system is out of control because the individual's mind is repetitively trying to refocus.

Imagine that one is looking at a scene and is constantly defocused, the brain says to refocus and still the image is unfocused. The 30 hertz pulsing is an in-phase system that compounds the unpleasantness of the experience due to the timing of the pulses.

It has been found in the subject invention that ten pulses per second to 100 pulses per second are affective in maintaining the defocusing at the retina. The result for the individual that has been irradiated is that the world becomes a vibrating fuzzy world in which nothing is in focus. The individual becomes disoriented because while the individual has not been rendered blind the world is now out of focus.

The result is disorientation and discomfort in which the individual's first response would be to cover his eyes. For instance all of a sudden data is not coming into the brain and one cannot for instance see a stop sign or aim ones weapon. Thus, the natural instinct is to stop what one is doing and cover ones eyes. Note also that by blinking one's eyes for a fraction of a second the cornea will cool down to a certain extent, but as soon as one opens one's eyes and one is still in the beam, defocusing will occur again.

In terms of pain, the subject system does not result in physical pain but rather psychological pain.

Note that the pulsed nature of the output of the laser is such that it does not heat up skin, whereas if it were a 100% duty cycle laser the 3° C. could reach 5° C., 8° C. and 10° C. and one would in fact feel the heat. The pulsed nature not only allows one a wide margin of eye safety control, it also allows phased deposition of energy that magnifies the defocusing affect. Invoking wavelength tunability as a source option would provide another control parameter on the outgoing radiation. Target distance and desired beam shaping to match situational requirements would further the desired effect over a larger projection area by selecting a wavelength where the dilution of fluence density absorbed per cornea could be adjusted by virtue of the cornea's absorbed energy determined by wavelength of the delivered energy.

The subject laser system could be for instance carried in a 30 pound backpack and be rifle sized, with the laser being laser diode energized. One would presumably need to carry about 250 to 300 watts as a prime electric power source in which rechargeable battery packs would be preferred.

In short, what is provided is a laser induced reduction of visual acuity suitable for crowd control and disabling of individuals through disorientation without permanently damaging or affecting the individual. This is accomplished in one embodiment by a pulsed IR source in the eye-safe laser region in which a laser beam is imaged onto the cornea of an individual to laterally differentially heat the cornea, thereby to cause defocusing and disorientation.

BRIEF DESCRIPTION OF THE DRAWINGS

These and other features of the subject invention will be better understood in connection with the Detailed Description, in conjunction with the Drawings, of which.

DETAILED DESCRIPTION

Figure 1:
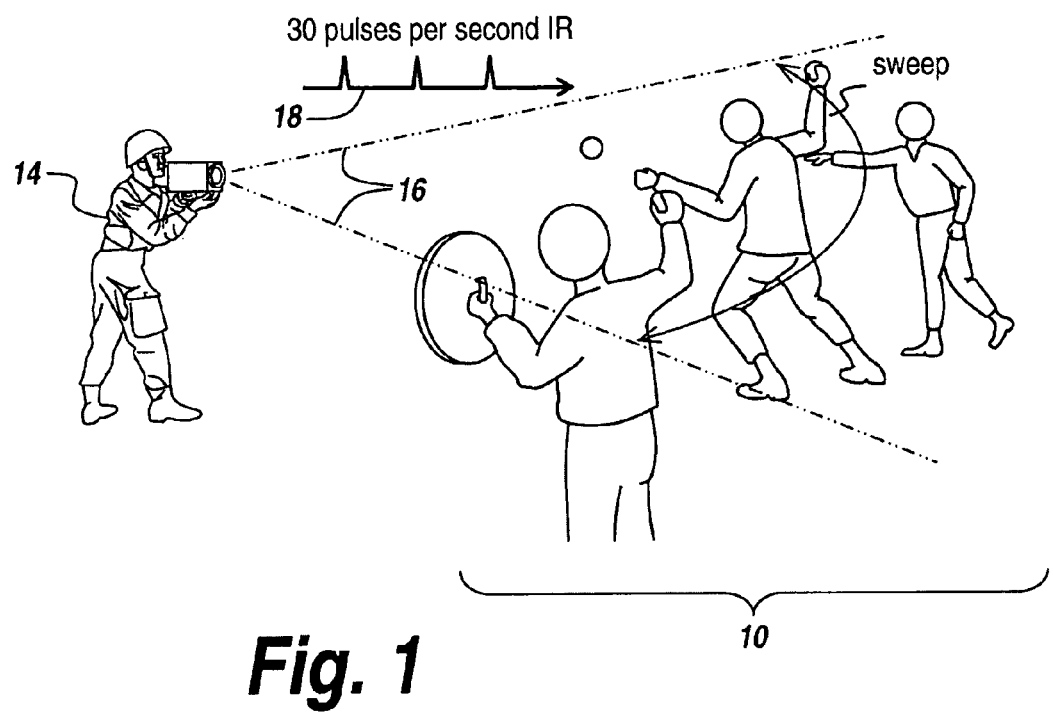
FIG. 1 is a diagrammatic illustration of the utilization of the subject system for immobilizing members of a crowd so as to disorient them with a series of pulses of infrared radiation that causes the irradiated individual to see images that are not in focus.

Referring now to FIG. 1, if one is to protect ones self against rabble 10 seeking to disrupt an individual 14 it is possible to disorient members of the rabble for preventing for instance throwing rocks, refuse and the like towards individual 14. This interdiction is accomplished by irradiating the corneas of the individuals with a laser beam 16 in the near infrared region of the electromagnetic spectrum, preferably between 2 and 3.5 microns, in which the laser beam is pulsed as illustrated by pulses 18.

When the pulsed laser beam absorbed is at the corneal surface over approximately 1 millimeter of depth the center of the cornea is raised by 3° C. in temperature with the deposit of a fluence of 0.2 j/cm$^2$ at $\alpha$=20 cm$^{-1}$, where $\alpha$ is the beam absorption coefficient at the projected radiation's wavelength. Note that the wavelength can be optimized for a higher $\alpha$ that requires less fluence, but which nonetheless has the same resulting image degradation.

The irradiation of the cornea deforms the cornea results in an aberration in the optical refractive power that degrades image quality at the retina. Moreover as the eye tries to accommodate, it cannot regain focus or refocus no matter what the autonomic nervous system tries to do. The result is blurred vision.

The subject system is designed for non-lethal suppression of potential or real combatants; and while traditional lasers operating in the visible spectrum have been utilized to distract or disable individuals, the visual signature exposes asset location.

Because of the subject laser operates in the eye-safe region, and because of the particular selection of the infrared wavelengths involved, one obtains retinal safe infrared wavelengths strongly absorbed by the ocular fluid or tissue before reaching the retina of the eye. Also due to the invisibility of the IR beam the system is a covert system.

Note that ocular defocus is induced by thermal alteration of the cornea surface shape such that significant defocus at eye-safe fluences occurs and such that discomfort, pain or disorientation results when the autonomic nervous system repeatedly attempts to focus the eye.

Figure 2:
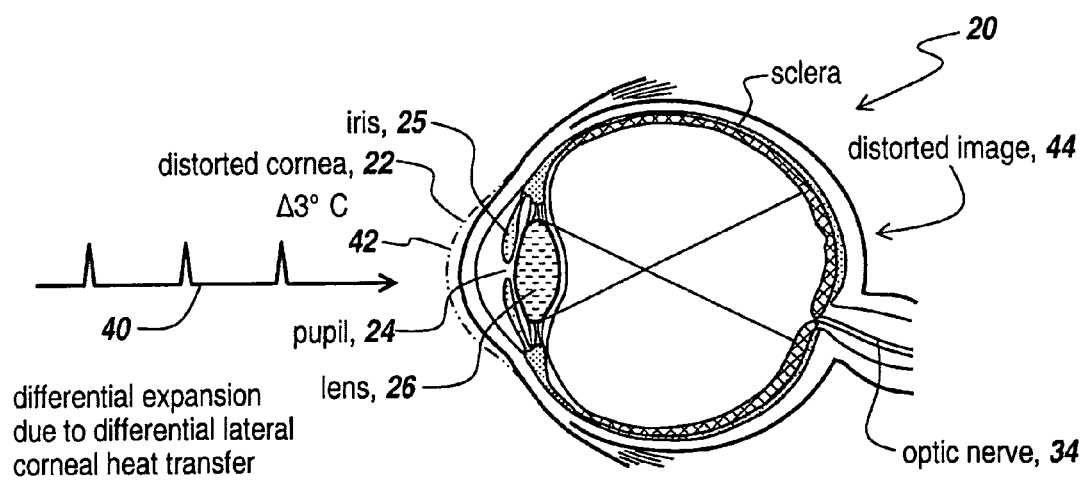
FIG. 2 is a diagrammatic illustration of the human eye illustrating the bulging or expansion of the center portion of a cornea upon irradiation with a pulsed infrared beam, thus to provide a distorted image at the retina of the eye due to differential expansion caused by differential lateral corneal heat transfer.

How the system works on the eye is now discussed. As can be seen in FIG. 2, a normal eye 20 has a cornea 22 which is positioned in front of pupil 24, iris 25 and lens 26.

The image formed by the optics described above exists at the retina 30, with the light having been focused through the vitreous humor 32 of the eye. This image is carried by the optic nerve 34 to the brain.

As can be seen by the wavetrain 40, when this wavetrain impinges upon cornea 22 the surface of the cornea shown in dotted outline at 42 expands non-linearly from the center of the cornea to its edges due to differential lateral corneal heat transfer. The result is a distorted image 44 at the retina which is the result of the defocusing due to the differential lateral corneal heat transfer.

Figure 3:
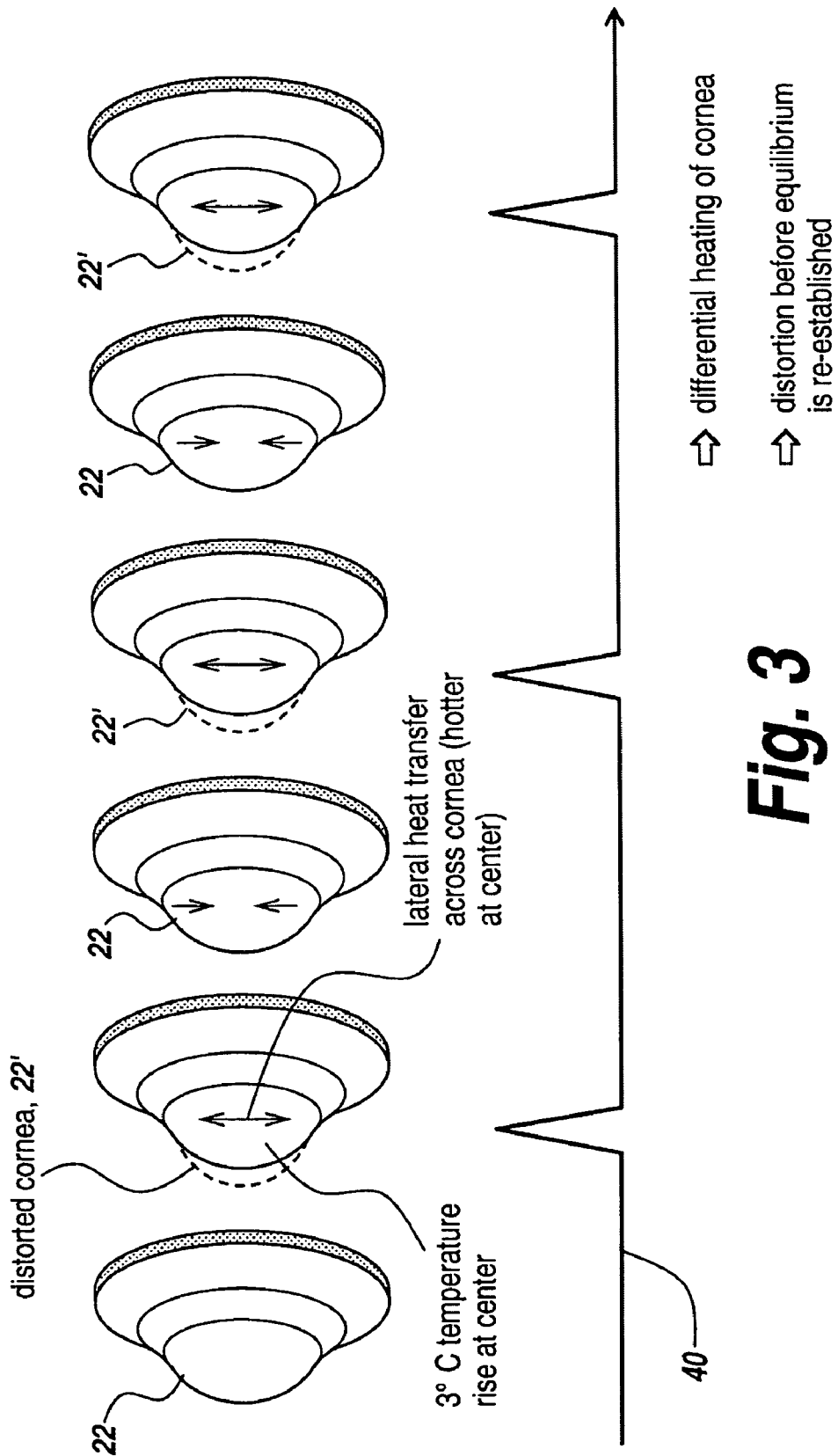
FIG. 3 is a diagrammatic illustration of a normal cornea having its center portion distorted through irradiation with pulse infrared energy to produce a 3° centigrade rise in temperature that causes differential heating of the cornea and subsequent distortion of the image focused by the lens behind the cornea.

Referring to FIG. 3, when a pulse wavetrain 40 impinges cornea 22 shown in its normal state, the cornea distorts as illustrated at 22' which as mentioned above is due to the lateral heat transfer across the cornea which will be hotter at its center than at its edges due to the fact that the edges of the cornea act as a heat sink. Therefore differential heating of the cornea occurs and distortion occurs before thermal equilibrium is reestablished across the cornea.

In one embodiment, the desired amount of heating is a rise of 3° centigrade at the center of the cornea.

It will be noted that the pulse repetition frequency of the pulses of wavetrain 40 is set such that just as the cornea reaches equilibrium after having been heated up by a pulse, another pulse heats the cornea.

Thus, the autonomic nervous system is unable to refocus the eye because the return to equilibrium is interrupted by another laser pulse. Thus the autonomic nervous system is continually trying to refocus the eye which it cannot do, causing major disorientation.

As will be described, the pulse repetition frequency is desirable between 10 to 100 pulses per second. However, 30 pulses per second corresponds both to the time that the cornea returns to equilibrium and also to the time that it takes the average eye to refocus. Thus this pulse repetition frequency has been found to accentuate the defocusing effect.

Figure 4:
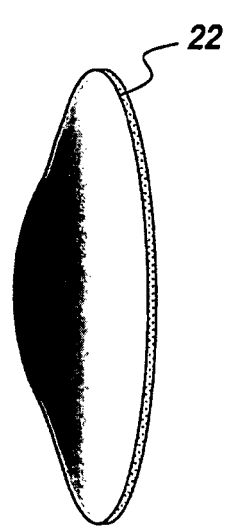
FIG. 4 is a diagrammatic illustration of a normal cornea at thermal equilibrium.
Figure 5:
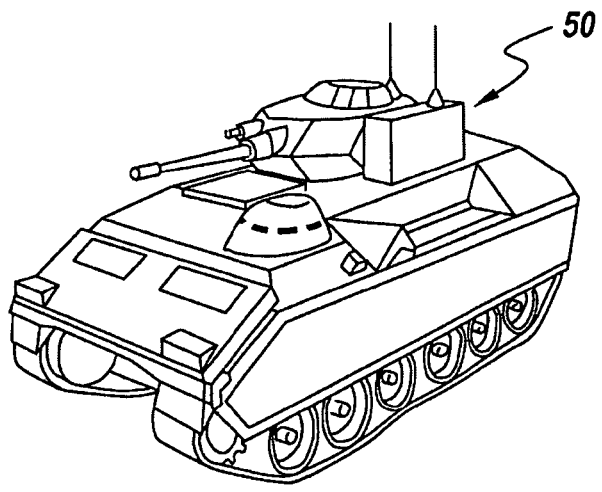
FIG. 5 is a photographic representation of an image focused by a lens through the normal cornea of FIG. 4, illustrating an in-focus condition.

Referring to FIG. 4, normal cornea 22 results in an image 50 at the retina of the eye.

Figure 6:
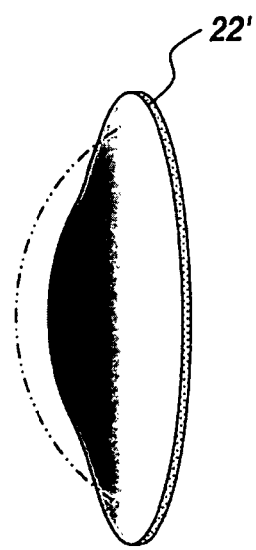
FIG. 6 is a diagrammatic illustration of a cornea having its surface altered through heating of the central portion thereof.
Figure 7:
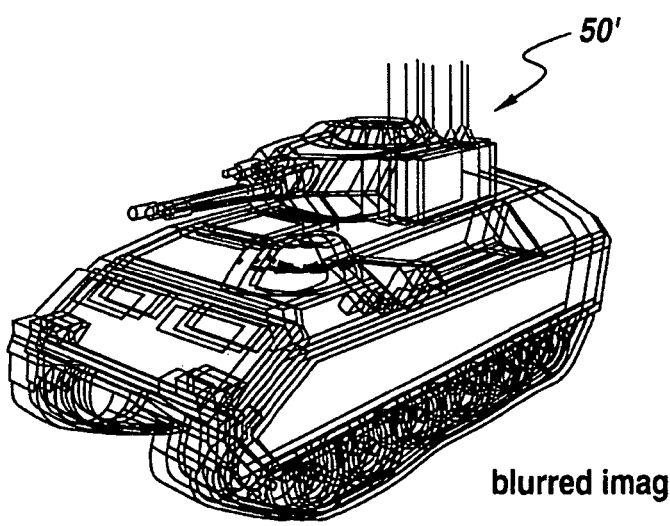
FIG. 7 is a photographic representation of the blurred image of FIG. 5 caused by the irradiation of the cornea.

As shown in FIG. 6, distorted cornea 22' results in a blurring of this image as shown at 50', thereby disorienting the individual irradiated by the laser beam.

As mentioned hereinbefore, the autonomic nervous system repeatedly tries to maintain focus or refocus the eye by adjusting the lens behind the cornea. This refocusing to provide a focused image would be effective if the temperature across the cornea were to reach equilibrium. It has been found that the eye refocuses in a cycle of approximately ⅓ second. After a nanosecond laser pulse has been delivered to the cornea, equilibrium starts to be reestablished. If reestablished at the end of ⅓ second then focus can be maintained.

However, the laser is pulsed to prevent equilibrium from being established. Thus, the reason for pulsing the laser is to make sure that the cornea does not reach equilibrium from which successful focusing can occur. Since the energy imparted to the surface of the cornea is nearly instantaneous, the next pulse of energy must be delivered before either equilibrium can occur or before the eye can refocus itself. For this reason a pulse repetition rate or frequency of 10 to 100 hertz has proven to be effective.

Figure 8:
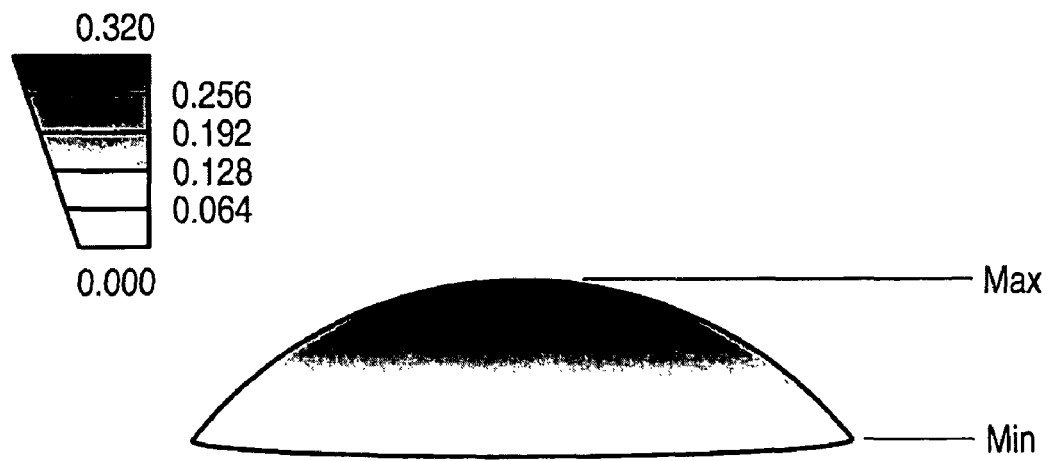
FIG. 8 is a diagrammatic illustration of a cornea indicating that the corneal curve provides ⅔rds of the eye's imaging power, with alteration of the cornea therefore significantly affecting focus.
Figure 8:
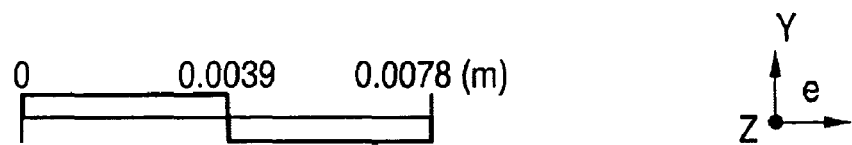

Referring to FIG. 8, in terms of the corneal curve, the top portion of the cornea provides ⅔ of the eye's imaging power. ⅔rds of the cornea therefore has a maximum effect on defocusing, whereas there is only a minimal effect on defocusing at the periphery at the cornea. This substantiates the fact that having the center of the cornea heated differentially with respect to the periphery provides a maximum amount of defocus.

Figure 9:
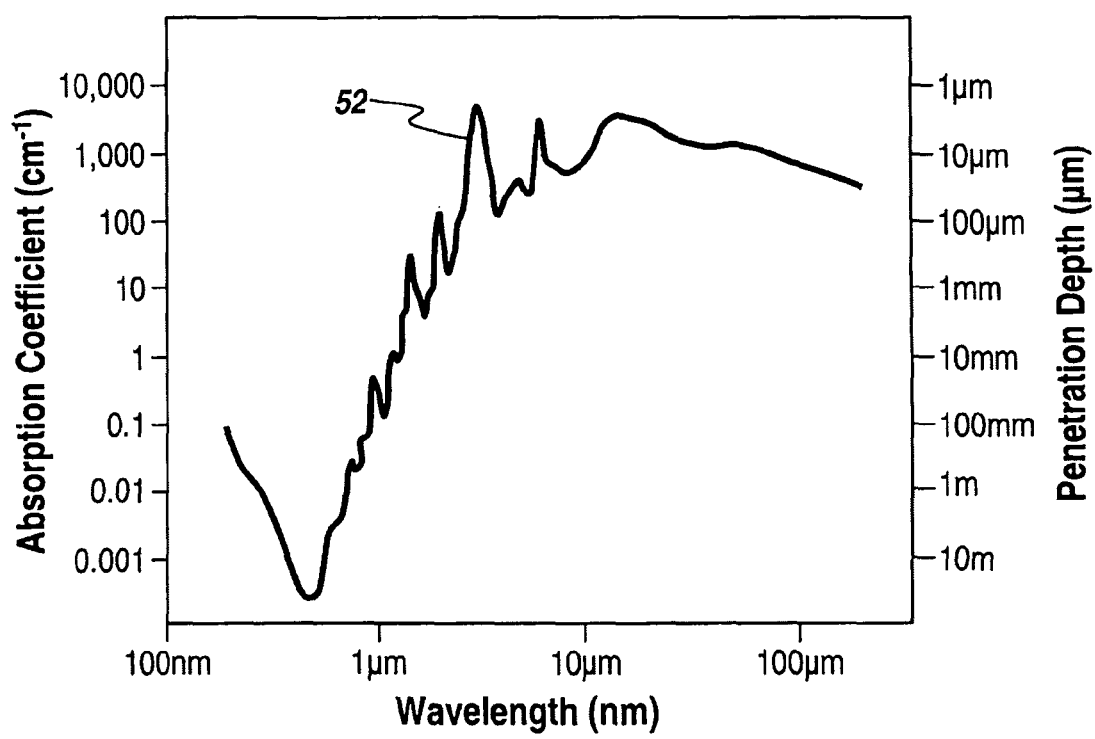
FIG. 9 is a graph showing absorption coefficient versus wavelength showing a peak of absorption at between 2 and 3.5 microns for the corneal material.

Referring to FIG. 9, the ocular attenuation is plotted against wavelength showing that in the eye-safe region, the optimum absorptive wavelength is between 2.5 and 3 microns. This is shown by the spike 52 in this absorption coefficient graph.

Figure 10:
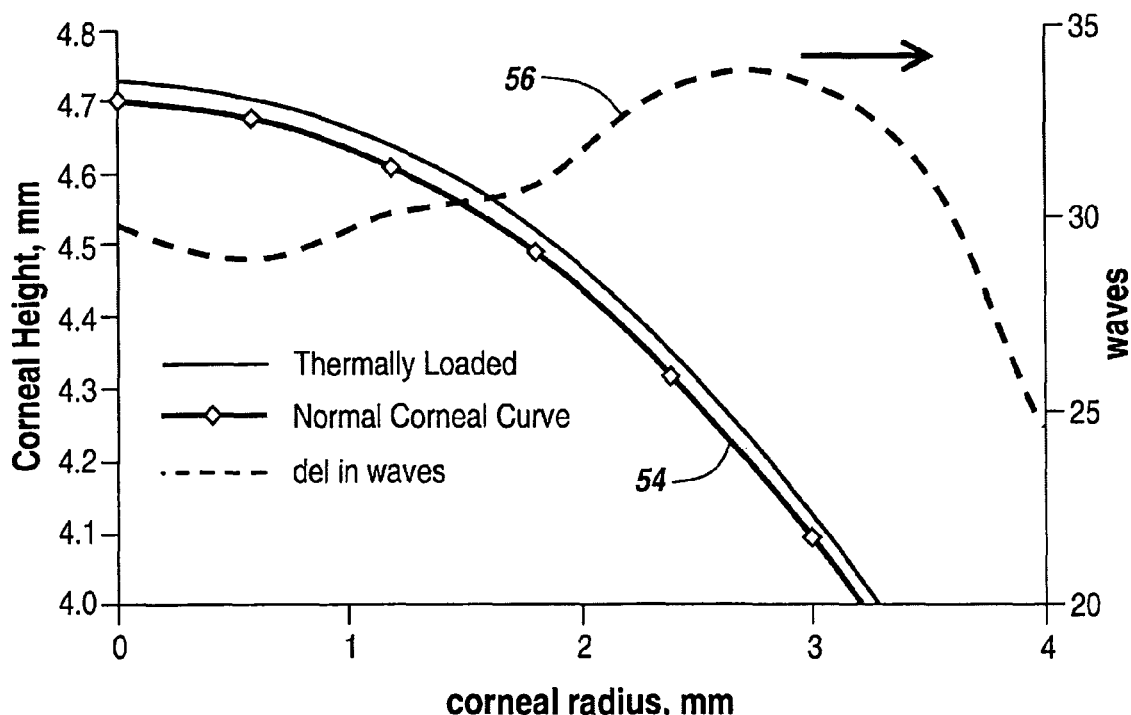
FIG. 10 is a graph of corneal reflective surface curve with and without thermal loading in millimeters illustrating a difference in wavelength at 0.589 nm showing a departure in the curve for the thermally loaded cornea.

Likewise referring to FIG. 10, corneal reflective surface curves, with and without thermal loading shown at 54 and 56, indicate substantial aberration of a thermally-loaded corneal surface with respect to the surface of an un-thermally loaded cornea. It can also be seen that the maximum corneal refractive surface aberration occurs at about 2.8 to 3 millimeters.

Figure 11:
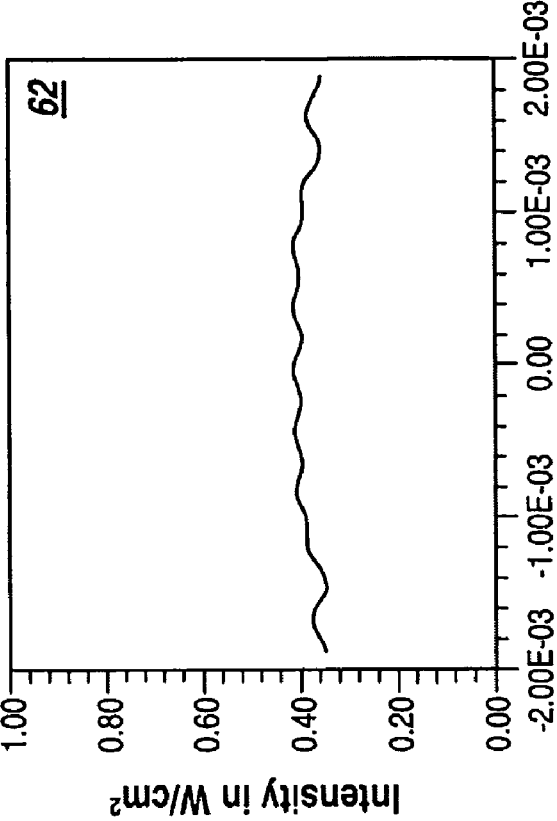
FIG. 11 is a series of two graphs of the response of the eye to an image having a grating in terms of the image plane on the retina and the same image of the grating with predicted spherical and defocused aberrations across the pupil indicating virtual zero acuity; and, FIG. 12 is a block diagram of the subject laser system.
Figure 11:
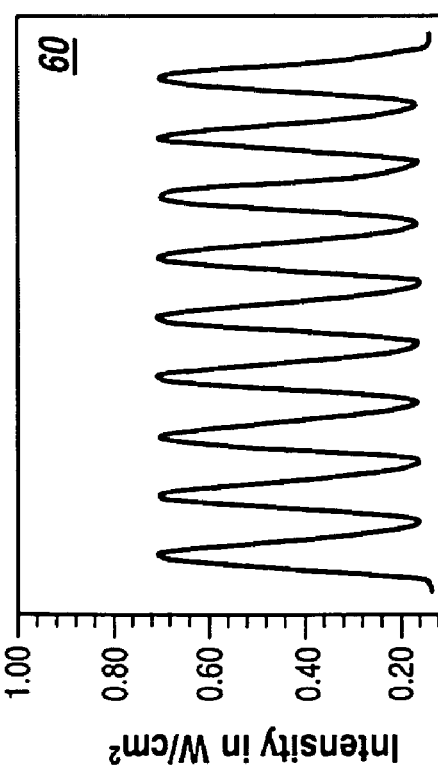

Finally, referring now to FIG. 11, two graphs are shown, namely graph 60 relating to the ability of the eye with a normal cornea to image a spatial diffraction grating and graph 62 showing the complete collapse of the ability of the eye to image the grating with a thermally distorted cornea.

A 2× Raleigh criteria MTF at the image plane on the retina in graph 60 shows pronounced peaks and valleys 64 and 66 which correspond to an in focus condition in which the lines of the spatial grating are resolved. Note, the thermal gradient at the cornea reduces acuity to nearly zero as shown in graph 62 in which the discerning of lines and spaces is completely absent.

Thus the subject laser induced reduction of visual acuity provides for disorientation of potential miscreants and forms a non-lethal suppression of potential or real combatants. The pulsed laser energy absorbed at the corneal surface results in a nominal 3° increase in temperature at the center of the cornea, with for instance 0.2 joules/cm$^2$ fluence given an α of 20 cm$^{-1}$.

As mentioned before, this results in deformed optical refractive power of the cornea which significantly degrades image quality. Moreover, when the eye tries to accommodate for the defocus it cannot refocus and a pulsed blurred vision results.

Retinal safe wavelengths are utilized and the fluence is kept below that which would raise the corneal temperature 10° C. to provide a safe non-lethal system. Moreover, because the system operates in the near infrared or mid-infrared region of the electromagnetic spectrum, those employing the lasers do not provide a visible signature that exposes their location.

Because of the differential heating across the cornea, the ocular defocus induced by the thermal alteration of the cornea surface shape significantly defocuses at eye-safe fluences and results in discomfort, pain or disorientation, with the autonomic nervous system repeatedly attempting to focus the eye.

Figure 12:
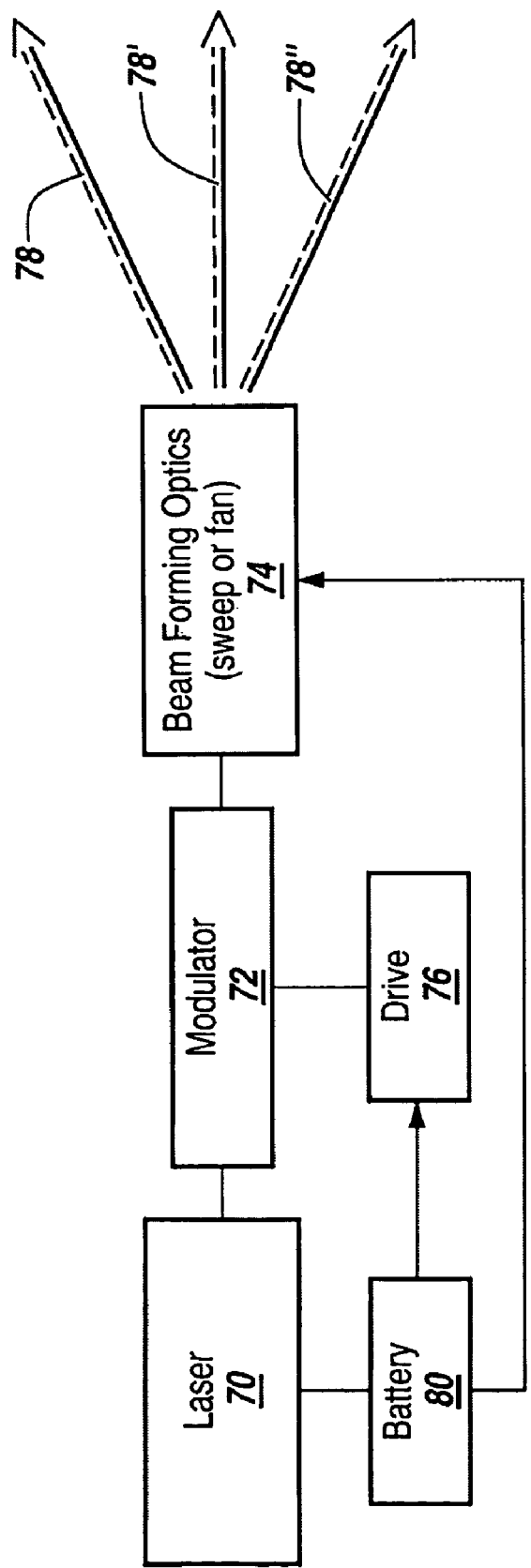

Referring now to FIG. 12, a block diagram of the subject system includes a laser 70, in one embodiment an erbium laser, which has its output coupled to a modulator 72, the output of which is coupled to a beam former 74. Modulator 72 is coupled to a drive 76 that provides control signals to the modulator so that a pulsed output is generated.

The beam forming optics may be either to provide a narrow diffraction-limited beam, a swept beam, or a fan shaped beam.

If a stationary pencil beam is desired, the apparatus may be mounted on a rifle stock so that the beam can be pointed at specific individuals and more importantly, their eyes. Beam formers and directors can be small enough to be mounted on a rifle sized version of the proposed concept.

Beam former 74 may include a piezoelectric element or one or more mirrors to repetitively sweep a beam as indicated at 78, 78', 78" at a crowd of people, or to sweep a predetermined sector.

The beam forming optics can also provide a fan of radiation to a predetermined sector, with the fan being lateral or vertical in extent so as to intercept a large number of individuals. Note also that the fan beam can subtend a vertical sector as well as a horizontal sector, so as to be able to interdict people of various heights.

In one embodiment, the subject system is intended to be portable and carry its own battery source shown at 80, with the apparatus being supported in a backpack or the like. In this portable embodiment the total weight of the apparatus is desirably limited to 30 pounds.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A non-destructive method for reducing the visual acuity of an individual to disorient the individual, comprising:

illuminating a cornea of the individual with only a pulsed infrared beam having insufficient energy to destroy corneal tissue but having sufficient energy to temporarily deform but not ablate such that the cornea is deformed with the impingement of the pulsed beam on the cornea due to the non-destructive heating of the ends of the cornea and such that visual acuity of the individual is impaired, whereby when the individual's autonomic nervous system seeks to refocus the individual's eye, the autonomic nervous system cannot do so, the individual therefore seeing a blurred image which disorients the individual.

2. The method of claim 1, wherein the pulsed infrared beam has a wavelength in the 2.5 to 3 micron range.

3. The method of claim 1, wherein the pulses in the beam have a pulse repetition rate and wherein the pulse repetition rate of the pulses in the beam is between 10 and 100 pulses per second.

4. The method of claim 1, wherein the pulses in the beam have a pulse repetition rate and wherein the pulse repetition rate is set to 30 pulses per second.

5. The method claim 1, wherein the pulses in the beam have a pulse repetition rate and wherein the pulse repetition rate is set to the time it takes for the autonomic nervous system to refocus the eye of the individual.

6. The method of claim 1, wherein the pulses in the beam have a pulse repetition rate and wherein the pulse repetition rate is set such that the pulse impinges on the cornea prior to the time that thermal equilibrium is established at the cornea.

7. The method of claim 1, wherein the pulses have fluence and wherein the fluence of the pulses is set such as to create a 3° C. rise in temperature at the center of the cornea upon the impingement on the cornea by a pulse, the temperature rise being insufficient to ablate the cornea.

8. The method of claim 1, wherein the pulses have an amount of energy and wherein the amount of pulsed energy delivered to the cornea is between 50 and 75 millijoules per square centimeter.

9. The method of claim 1, wherein the pulses have an amount of energy and wherein the amount of pulsed energy imparted to the cornea to promote defocusing of a person is on the order of 100 millijoules per square centimeter.

10. The method of claim 1, wherein the pulsed beam is generated by an erbium laser.

11. The method of claim 10, wherein the beam from the laser is fanned out.

12. The method of claim 11, wherein the fanning out of the beam from the laser is accomplished utilizing an optical fanning element.

13. The method of claim 11, wherein the fanning of the beam is created through the use of a piezoelectric element.

14. The method of claim 11, wherein the fanning of the beam is created by movable mirrors.

15. A non-destructive method for disorienting an individual comprising causing the individual discomfort by irradiating the a cornea of an individual with only a series of pulsed infrared pulses in a laser beam; to temporarily deform the cornea without ablation and cause periodic blurring of images at the retina of the individual, the pulse repetition rate of the pulses being such as to defeat the action of the autonomic nervous system of the individual to refocus the eye of the individual.

\* \* \* \* \*